United States Patent [19]

Rauleder et al.

[11] Patent Number: 4,562,274

[45] Date of Patent: Dec. 31, 1985

[54] PROCESS FOR THE PREPARATION AND ISOLATION OF POLYGLYCIDYL COMPOUNDS

[75] Inventors: Gebhard Rauleder, Belford Roxo, Brazil; Helmut Waldmann, Leverkusen, Fed. Rep. of Germany; Ludwig Bottenbruch; Hans-Joachim Traenckner, both of Krefeld, Fed. Rep. of Germany; Wolfgang Gau, Wuppertal, Fed. Rep. of Germany

[73] Assignee: Bayer Aktiengesellschaft, Leverkusen, Fed. Rep. of Germany

[21] Appl. No.: 560,358

[22] Filed: Dec. 12, 1983

[30] Foreign Application Priority Data

Dec. 21, 1982 [DE] Fed. Rep. of Germany ....... 3247255

[51] Int. Cl.$^4$ ................... C07D 301/14; C07D 301/32
[52] U.S. Cl. .................... 549/525; 549/541; 544/219; 544/221
[58] Field of Search ............... 549/541, 525; 544/219, 544/221

[56] References Cited

U.S. PATENT DOCUMENTS

| Re. 30,945 | 5/1982 | Prescher et al. | 549/525 |
|---|---|---|---|
| 3,254,097 | 5/1966 | Darrow | 549/541 |
| 3,920,708 | 11/1975 | Kubo et al. | 549/541 |

FOREIGN PATENT DOCUMENTS

| 8111 | 2/1980 | European Pat. Off. | 549/525 |
|---|---|---|---|
| 8112 | 2/1980 | European Pat. Off. | 549/525 |
| 8114 | 2/1980 | European Pat. Off. | 549/525 |
| 8115 | 2/1980 | European Pat. Off. | 549/525 |
| 8116 | 2/1980 | European Pat. Off. | 549/525 |
| 0056932 | 8/1982 | European Pat. Off. . | |
| 1953465 | 6/1970 | Fed. Rep. of Germany . | |
| 1942557 | 3/1971 | Fed. Rep. of Germany . | |
| 1643852 | 5/1971 | Fed. Rep. of Germany . | |
| 2023839 | 11/1971 | Fed. Rep. of Germany . | |
| 2747761 | 4/1978 | Fed. Rep. of Germany . | |
| 2747762 | 4/1978 | Fed. Rep. of Germany . | |

OTHER PUBLICATIONS

Chemical Abstracts, vol. 90, No. 10, Mar. 1979, Abstract-No. 72 831c.

Primary Examiner—Norma S. Milestone
Attorney, Agent, or Firm—Sprung Horn Kramer & Woods

[57] ABSTRACT

Polyglycidyl compounds are prepared by reacting certain polyallyl compounds with a percarboxylic acid containing 3 or 4 C atoms, subsequently removing, by distillation, the carboxylic acid formed from the percarboxylic acid, then separating the remaining mixture by simultaneous extraction with a lipophilic and a hydrophilic phase, subsequently working up the laden lipophilic phase and the laden hydrophilic phase separately in a manner which is known per se, and obtaining the polyglycidyl compound as the residue from working up of the laden hydrophilic phase.

8 Claims, No Drawings

PROCESS FOR THE PREPARATION AND ISOLATION OF POLYGLYCIDYL COMPOUNDS

The present invention relates to a process for the preparation of polyglycidyl compounds from polyallyl compounds and percarboxylic acids and to the isolation of the polyglycidyl compounds from the reaction mixtures thereby obtained.

The polyglycidyl compounds which can be prepared and isolated according to the invention are known intermediates and are used, for example, as starting substances for the preparation of lacquers and plastics, as stabilizers, for the preparation of casting resins, for the preparation of open-air insulators, as plasticizers and as adhesives (see, for example, German Auslegeschrift No. 1,082,263 and U.S. Pat. No. 2,870,170).

It is known that glycidyl esters can be prepared from carboxylic acids, carboxylic anhydrides and salts of carboxylic acids by reaction with epihalogenohydrin (see, for example, German Auslegeschrift No. 1,165,030, German Offenlegungsschrift No. 1,643,777, U.S. Pat. No. 2,448,602 and German Offenlegungsschrift No. 2,023,148). A fundamental disadvantage of these processes is that salt-containing effluents which pollute the environment are formed.

British Patent Specification No. 735,001 describes the preparation of glycidyl esters by reaction of glycidol with polycarboxylic acid chlorides. This process has the great disadvantage that the starting materials are unstable and very reactive, so that extreme care is necessary during the preparation, storage and use of these compounds (see German Offenlegungsschrift No. 2,032,148, page 1, line 6).

One possibility of converting olefins into epoxides avoiding these disadvantages is to apply the "Prileschajew reaction" (compare N. Prileschajew, Ber. dtsch. chem. Ges. 42, 4811 (1909)). This reaction is an electrophilic attack of a percarboxylic acid on an olefine (compare K. D. Bingham, G. D. Meakins and G. H. Witham, Chem. Comm. 1966, pages 445 and 446). For this reason, the reactivity of the olefine decreases as the nucleophilic character of the double bond decreases. Electronegative substituents therefore impede the epoxidation (compare S. N. Lewis in R. L. Augustin, "Oxidation" Volume I, page 227, lines 9-13, Marcel Dekker, New York (1969)).

Electron-withdrawing groups, such as, for example, carboxyl, carbonyl and the like, greatly reduce the rate of reaction (compare H. Batzer and E. Nikles, Chimia, Volume 16, page 62 (1962)). In particular, allyl compounds therefore cannot be epoxidized with percarboxylic acids without problems (compare German Offenlegungsschrift No. 2,023,148). As a result of the low reactivity of their double bond, high temperatures and long reaction times are required, which gives rise to the formation of undesirable by-products, such as dihydroxy and hydroxyacyloxy derivatives of the starting substances (compare S. N. Lewis in R. L. Augustin, "Oxidation" Volume I, page 233, lines 6-11, Marcel Dekker, New York (1969)).

British Patent Specification No. 862,588 proposes epoxidation of the allyl ester of terephthalic acid with 50% strength hydrogen peroxide in the presence of a cation exchanger containing adsorbed acetic acid (compare page 2, line 15). However, the use of a cation exchanger as a catalyst has the disadvantage that it is attacked by the reaction mixture, so that the possibility of repeated use is only limited (compare German Auslegeschrift No. 1,082,263, page 1, line 40).

Example 9, page 8, line 40 of German Auslegeschrift No. 1,082,263 describes the epoxidation of diallyl terephthalate with peracetic acid, prepared "in situ", in the presence of aluminum oxide. However, the large amount of solid catalyst in the reaction mixture (70 g of aluminum oxide per mol of diallyl terephthalate) presents a particular disadvantage for industrial application. When the reaction has ended, the catalyst must be separated off from the reaction mixture, purified and regenerated, the number of times it can be re-used being very limited.

Two further patent specifications (U.S. Pat. No. 3,155,638 and French Patent Specification No. 1,394,195) propose the use of monoperphthalic acid for the epoxidation of ethylenically unsaturated carboxylic acid esters. A disadvantage of this method is, however, the technically complicated recovery of the phthalic acid from the reaction mixture. Thus, Example 11, pages 8 and 9 of U.S. Pat. No.3,155,638 describes removal by filtration of the deposited phthalic acid after the reaction of diallyl phthalate with phthalic anhydride and hydrogen peroxide. The residue remaining in the filtrate must be recovered by repeated washing with water and sodium hydroxide solution and the aqueous phases must then be acidified again in order to recover the phthalic acid contained therein, which leads to the formation of undesirable waste salts. In Example 12 of this U.S. Patent Specification, diallyl maleate is reacted with phthalic anhydride and hydrogen peroxide. After the same working up procedure as that described above, allyl glycidyl maleate results in a yield of only 24% of theory. No diglycidyl maleate has been obtained.

The use of m-chloroperbenzoic acid for epoxidation of the allyl esters of polycarboxylic acids, as has been proposed in the literature (S. R. Sandler and F. R. Berg, J. Chem. and Eng. Data, Volume 11, pages 447 and 448 (1966)) is also unsuitable for industrial application, since the proposed reaction conditions of 3° to 5° C. necessitate the use of expensive cooling brines, and the stated reaction time of 3 days is unacceptable in industry. In spite of these involved reaction conditions, diglycidyl terephthalate, for example, has been obtained in a yield of only 28% of theory (compare page 448, line 13).

Examples 1 to 5 and Example 8 of U.S. Pat. No. 2,761,870 describe the epoxidation of crotyl esters of carboxylic acids with 45% strength peracetic acid. In this case also, the reaction conditions—the reaction mixture must stand at 0° to 25° C. for 2 days, are extremely expensive for industrial application (use of cooling brines, long reaction time). After the reaction, the acetic acid is removed from the reaction mixture by washing with 20% strength sodium hydroxide solution. If the acetic acid is to be recovered, the aqueous phase must be acidified again, which leads to waste salts which pollute the environment.

In U.S. Pat. No. 3,155,638, Example 13, the phthalic acid is filtered off after the reaction of diallyl fumarate with phthalic anhydride and hydrogen peroxide. The residue which remains in the filtrate must be recovered by repeated washing with sodium hydroxide solution and water, and the aqueous phases must then be acidified again in order to recover the phthalic acid contained therein, which leads to the formation of undesirable waste salts. Only allyl glycidyl fumarate is obtained in this process, and then only in a yield of 34% of theory.

The reaction of diallyl maleate with peracetic acid is reported in J. Am. Chem. Soc. 81, page 3354 (1959). In spite of a 4-fold excess of ester, the reaction time was 11.5 hours at 50° C. Allyl glycidyl maleate was obtained in a yield of only 71%. The preparation of diglycidyl maleate is not mentioned.

Example 2 of U.S. Pat. No. 2,783,250 describes the preparation of diallyl tetrahydrophthalate with peracetic acid in chloroform. After a reaction time of 10 hours at 0° to 10° C., a highly viscous residue which was identified as allyl 7-oxabicyclo-(4.1.0)-heptane-3,4-carboxylate was obtained after removal of the acetic acid and solvent.

Example 1 of U.S. Pat. No. 2,870,170 describes the reaction of diallyl tetrahydrophthalate with peracetic acid in chloroform. After a reaction time of 2 days at 0° to 10° C., a residue which was identified as allyl glycidyl 7-oxabicyclo-(4.1.0)-heptane-3,4-dicarboxylate was obtained after removal of the acetic acid and the solvent. The yield was 50% of theory.

A process has now been found for the preparation of polyglycidyl compounds, which is characterized in that a polyallyl compound of the general formula

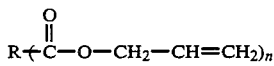

$$R\!+\!\!\overset{\overset{\displaystyle O}{\|}}{C}\!-\!O\!-\!CH_2\!-\!CH\!=\!CH_2)_n$$

wherein
R represents an optionally substituted, saturated aliphatic radical with 1 to 10 C atoms, the group —CH=CH—, an optionally substituted, saturated or unsaturated cycloaliphatic radical with 5 to 12 C atoms, an optionally substituted benzene radical or an optionally substituted naphthalene radical and
n represents 2, 3 or 4,
or a triallyl compound of cyanuric acid, isocyanuric acid or urazole, is reacted with a percarboxylic acid containing 3 or 4 carbon atoms, subsequently removing, by distillation, the carboxylic acid formed from the percarboxylic acid, then separating the remaining mixture by simultaneous extraction with a lipophilic and a hydrophilic phase, subsequently working up the laden lipophilic phase and the laden hydrophilic phase separately in a manner which is known per se, and obtaining the polyglycidyl compound as the residue from working up of the laden hydrophilic phase.

If a compound of the above general formula is used as the polyallyl compound, the radical R, if this is substituted, can contain, as substituents, for example, $C_1$- to $C_4$-alkyl and/or $C_1$- to $C_4$-alkoxy groups. In the above general formula, n preferably represents 2 or 3.

Examples of polyallyl compounds which are suitable for use in the process according to the invention are the polyallyl esters of hexahydrophthalic acid, hexahydroisophthalic acid, hexahydroterephthalic acid, 3-methylhexahydrophthalic acid, 3,5-dimethylhexahydrophthalic acid, hydrogenated benzene-tri- and -tetracarboxylic acids, tetrahydrophthalic acid, 3-methylphthalic acid, 3,5-dimethylphthalic acid, 3-methoxyphthalic acid, terephthalic acid, benzenetricarboxylic acids, benzenetetracarboxylic acids, naphthalenedicarboxylic acids, malonic acid, succinic acid, glutaric acid, adipic acid, pimelic acid, suberic acid, decanedicarboxylic acid, maleic acid and fumaric acid and the trisallyl compounds of cyanuric acid, isocyanuric acid and urazole.

The diallyl esters of 3-methyl-hexahydrophthalic acid, 3-methoxy-hexahydrophthalic acid, hexahydrophthalic acid, hexahydroisophthalic acid, hexahydroterephthalic acid, methylphthalic acid, phthalic acid, terephthalic acid, tetrahydrophthalic acid, malonic acid, succinic acid, glutaric acid, adipic acid, maleic acid and fumaric acid and the trisallyl compounds of isocyanuric acid and urazole are particularly suitable for the reaction with percarboxylic acids by the process according to the invention.

The diallyl esters of hexahydrophthalic acid, hexahydroterephthalic acid, tetrahydrophthalic acid, phthalic acid, malonic acid, succinic acid, glutaric acid, adipic acid, maleic acid and fumaric acid and the trisallyl compounds of isocyanuric acid and urazole are especially suitable for use in the process according to the invention.

The polycarboxylic acid polyallyl esters which can be used in the process according to the invention can be obtained in a manner which is known per se, for example by esterification of the corresponding acid anhydrides or acids with allyl alcohol. The trisallyl compounds of cyanuric acid, isocyanuric acid and urazole can be obtained, for example, by reacting these compounds with allyl chloride.

The reaction with the percarboxylic acid is preferably carried out in the presence of an organic solvent. Organic solvents which can be used are the most diverse unsubstituted and substituted hydrocarbons which are liquid under the reaction conditions and undergo only very minor undesirable side reactions or none at all. Examples of hydrocarbons which can be used are: aliphatic and cycloaliphatic hydrocarbons, such as hexane, heptane, octane, 2-ethyl-hexane, decane, dodecane, cyclohexane, methylcyclopentane and petroleum ether, and furthermore aromatic hydrocarbons, such as benzene, nitrobenzene, toluene, ethylbenzene, cumene, diisopropylbenzene, xylene, chlorobenzene and dichlorobenzene, as well as oxygen-containing hydrocarbons, such as diethyl ether, diisopropyl ether, dibutyl ether, tetrahydrofuran, dioxane, ethyl acetate, methyl acetate, propyl acetate, butyl acetate, methyl propionate, ethyl propionate, propyl propionate, methyl butyrate, ethyl butyrate, propyl butyrate, butyl butyrate, methyl benzoate and ethyl benzoate, and moreover chlorinated hydrocarbons, such as methylene chloride, chloroform, carbon tetrachloride, 1-chloroethane, 1,2-dichloroethane, 1,1-dichloroethane, 1,1,2,2-tetrachloroethane, 1-chloropropane, 2-chloropropane, 1,2-dichloropropane, 1,3-dichloropropane, 2,3-dichloropropane, 1,2,3-trichloropropane, 1,1,2,3-tetrachloropropane, butyl chloride, 1,2-dichlorobutane, 1,4-dichlorobutane, 2,3-dichlorobutane, 1,3-dichlorobutane, 1,2,3,4-tetrachlorobutane, tert.-butyl chloride, amyl chloride, 1,2-dichloropentane, 1,5-dichloropentane, 1,2,3,4-tetrachloropentane, cyclopentyl chloride, 1,2-dichlorocyclopentyl chloride, hexyl chloride, 1,2-dichlorohexane, 1,6-dichlorohexane, 1,2,3,4-tetrachlorohexane, 1,2,5,6-tetrachlorohexane, cyclohexyl chloride, chlorobenzene, heptyl chloride, 1,2-dichloroheptane, 1,2,3,4-tetrachloroheptane, cycloheptyl chloride, octyl chloride, 1,2-dichlorooctane, 1,2,3,4-tetrachlorooctane and cyclooctyl chloride.

Preferred solvents are, of the chlorinated hydrocarbons: methylene chloride, chloroform, carbon tetrachloride and 1,2-dichloropropane; of the aromatic hydrocarbons: benzene, nitrobenzene, toluene, chlorobenzene and dichlorobenzene; of the aliphatic and cycloaliphatic hydrocarbons: 2-ethyl-hexane, cyclohexane and methylcyclopentane; and of the oxygen-containing hydrocarbons: tetrahydrofuran, ethyl propionate and ethyl benzoate.

Particularly preferred solvents are, of the chlorinated hydrocarbons: 1,2-dichloropropane and carbon tetrachloride; of the aromatic hydrocarbons: benzene and dichlorobenzene; of the aliphatic and cycloaliphatic hydrocarbons: cyclohexane; and of the oxygen-containing hydrocarbons: ethyl propionate.

Mixtures of the various organic solvents mentioned above can also be used.

Percarboxylic acids which can be used in the process of the present invention are perpropionic acid, perbutyric acid and perisobutyric acid. Perpropionic acid and perisobutyric acid are preferably used, and perpropionic acid is particularly preferred.

These percarboxylic acids, dissolved in one of the organic solvents, mentioned, can be prepared, for example, by the process described in German Offenlegungsschrift No. 2,262,970, in which aqueous hydrogen peroxide is reacted with the corresponding carboxylic acid in the presence of sulphuric acid and the resulting percarboxylic acid is then extracted from the reaction mixture with an organic solvent. If appropriate, the resulting solution of the percarboxylic acid in the organic solvent can be purified further, for example in order to reduce the content of water, hydrogen peroxide and sulphuric acid.

The percarboxylic acid is generally used in the form of a solution in an organic solvent. Such percarboxylic acid solutions can contain, for example, 10 to 30% by weight of the particular percarboxylic acid, based on the solution. The polyallyl compounds can be used as such or likewise dissolved in one or more of the above-mentioned solvents, it being possible to use solutions of any desired concentration of the polyallyl compounds. Preferably, the polyallyl compounds are used as such and organic solvents are added only in the form of the percarboxylic acid solution.

0.6 to 1.1 mol of percarboxylic acid, for example, can be used per mol of double bond to be epoxidized. 0.7 to 1 mol of percarboxylic acid is preferably used per mol of double bond to be epoxidized, particularly preferably 0.75 to 0.9 mol of percarboxylic acid per mol of double bond to be epoxidised.

The water content of the percarboxylic acid solution used should in general be as low as possible. Amounts of water up to 10% by weight in the percarboxylic acid solution generally cause no problems. A percarboxylic acid solution with a water content of, for example, up to 2% by weight is suitable. A percarboxylic acid solution containing less than 1% by weight of water is preferably used. A water content of less than 0.1% by weight is particularly preferred.

The hydrogen peroxide content of the solution of the percarboxylic acid used in one of the abovementioned organic solvents should generally be as low as possible. It can be, for example, up to 1% by weight, based on the percarboxylic acid solution. The content is advantageously less than 0.5% by weight. It is particularly advantageous to carry out the reaction with a percarboxylic acid solution having a hydrogen peroxide content of less than 0.2% by weight.

The mineral acid content of the percarboxylic acid solution used should be as low as possible. It is advantageous to carry out the reaction with a percarboxylic acid solution having a mineral acid content of less than 50 ppm. A mineral acid content of less than 10 ppm is particularly advantageous.

The reaction according to the invention is carried out, for example, in the temperature range from 30° to 100° C. It is preferably carried out at 40° to 80° C. and particularly preferably at 50° to 75° C. In particular cases, the temperature can also be below or above those given.

Besides using a procedure under isothermal conditions, that is to say maintaining a uniform temperature in the entire reaction mixture, the reaction according to the invention can also be carried out with development of a so-called temperature gradient, which in general increases as the reaction progresses. However, it is also possible to carry out the reaction such that a gradient of decreasing temperature develops as the reaction progresses.

The reaction according to the invention can be carried out under the most diverse pressures. In general, it is carried out under normal pressure. However, the reaction can also be carried out under reduced or increased pressure.

The reaction according to the invention can be carried out discontinuously or continuously in the customary devices for reactions of this type, such as stirred kettles, boiling reactors, tube reactors, loop reactors or circulatory reactors.

Examples of materials which can be used for the reaction apparatus for carrying out the reaction according to the invention are glass, stainless steels or enamelled material.

Heavy metal ions in the reaction mixture catalyze the decomposition of the percarboxylic acid. Substances which can inactivate heavy metal ions by complex formation are therefore generally added to the percarboxylic acid solution. Examples of known substances of this type are gluconic acid, ethylenediaminetetraacetic acid, sodium silicate, sodium pyrophosphate, sodium hexametaphosphate, disodium dimethyl-pyrophosphate or $Na_2(2\text{-ethylhexyl})_5(P_3O_{10})_2$ (compare German Auslegeschrift No. 1,056,596, column 4, line 60 et seq.).

The heat of reaction can be removed by internal or external coolers. The reaction can also be carried out under reflux in order to remove the heat of reaction (for example in boiling reactors).

The polyallyl compound and the percarboxylic acid can be brought together in any desired manner. For example, the two components can be introduced simultaneously or successively in any desired sequence into the reaction vessel. In the discontinuous procedure, the polyallyl compound is preferably initially introduced and the percarboxylic acid solution is added. The reaction temperature can thereby be established before or after addition of the percarboxylic acid. It is also possible to introduce the two components into the reaction vessel together at room temperature and then to establish the reaction temperature. In the continuous procedure, the two components can be fed to the reactor together or separately. If several reactors are used, it being possible for these to be connected, for example, in series as a cascade, it may be advantageous to introduce the polyallyl compounds only into the first reactor. However, the polyallyl compound can also be fed into several reactors.

It may furthermore be advantageous to add the required amount of percarboxylic acid batchwise. It may also be advantageous here to remove the carboxylic acid formed from the percarboxylic acid from the reaction mixture after the addition of individual batches.

The reaction mixtures obtained after carrying out the reaction according to the invention in general contain the organic solvent used, the carboxylic acid formed from the percarboxylic acid, unreacted polyallyl compound, partially epoxidized polyallyl compound, completely epoxidized polyallyl compound (=polyglycidyl compound) and, where relevant, small amounts of high-boiling by-products.

For working up, the carboxylic acid formed from the percarboxylic acid is first removed from the reaction mixture by distillation. This distillation is preferably carried out in the presence of a solvent having a boiling point between that of the carboxylic acid formed from the percarboxylic acid and that of the polyallyl compound, in which case a top product containing the solvent and the carboxylic acid and a bottom product containing the unreacted polyallyl compound, partially epoxidized polyallyl compound, polyglycidyl compound and residual solvent are separated off.

If a solvent of suitable boiling point has been used for the percarboxylic acid, separate addition of a solvent can be omitted. Otherwise, it is advantageous to add a further solvent having a boiling point between that of the carboxylic acid formed from the percarboxylic acid and that of the polyallyl compound before the distillation, for example in an amount of 20 to 100% by weight, based on the reaction mixture. This amount is preferably 30 to 80% by weight. If a further solvent is used, any solvent which may have been introduced with the percarboxylic acid is generally entirely in the top product, and the bottom product then contains only residues of the further solvent.

This distillation can be carried out, for example, under a pressure in the range from 100 to 400 mbar and at a bottom temperature in the range from 90° to 140° C.

Complete removal of the carboxylic acid at relatively low bottom temperatures can generally be achieved by the preferred procedure in the presence of an auxiliary solvent, this being advantageous in respect of minimizing the formation of by-products from the carboxylic acid and the epoxidized constituents of the reaction mixture.

Examples of suitable auxiliary solvents are dichlorobenzene, ethyl benzoate, diethylene glycol diethyl ether and diethylene glycol dimethyl ether. Dichlorobenzene is preferably used for this.

It may be advantageous for stabilizers which can prevent the formation of high-boiling compounds and polymers to be added to the reaction mixture before or during this working up by distillation.

To isolate the polyglycidyl compound from the reaction mixture remaining after the distillation, this mixture being free from carboxylic acid and at least substantially free from solvent, the mixture is separated by simultaneous extraction with a lipophilic and a hydrophilic phase. A lipophilic phase of cycloalkanes, such as cyclohexane or methylcyclopentane, or of mixtures of 60 to 90% by weight of alkanes with 5 to 12 C atoms or 60 to 90% by weight of cycloalkanes and in each case 10 to 40% by weight of benzene, toluene, xylene, chlorobenzene, dichlorobenzene, chloroform, butyl acetate or tetrahydrofuran, and a hydrophilic phase of ethylene glycol, diethylene glycol, sulpholane or N-methylpyrrolidone or of mixtures of 30 to 80% by weight of water and 20 to 70% by weight of methanol, ethanol or isopropanol, or of mixtures of 10 to 25% by weight of water and 75 to 90% by weight of ethylene glycol, diethylene glycol or sulpholane, or of mixtures of 10 to 80% by weight of water and 20 to 90% by weight of N-methylpyrrolidone, or of mixtures of 50 to 90% by weight of ethylene glycol and 10 to 50% by weight of methanol, ethanol or isopropanol, are preferably used.

A lipophilic phase of cyclohexane or methylcyclohexane or of mixtures of 60 to 90% by weight of alkanes with 5 to 12 C atoms or 60 to 90% by weight of cycloalkanes and in each case 10 to 40% by weight of benzene, dichlorobenzene, chloroform or tetrahydrofuran, and a hydrophilic phase of ethylene glycol, diethylene glycol, sulpholane or N-methylpyrrolidone or of mixtures of 30 to 50% by weight of water and 50 to 70% by weight of methanol, ethanol or isopropanol, or of mixtures of 75 to 90% by weight of sulpholane and 10 to 25% by weight of water, or of mixtures of 50 to 80% by weight of N-methylpyrrolidone and 20 to 50% by weight of water, are particularly preferably used.

Mixtures consisting of 30 to 50% by weight of water and 50 to 70% by weight of methanol or N-methylpyrrolidone are generally very particularly preferred for the formation of the hydrophilic phase. In individual cases, the water content here can be up to 80% by weight, thus, for example, in the separation of the reaction components from the reaction of percarboxylic acid with trisallylurazole. Cyclohexane or mixtures consisting of 60 to 90% by weight of alkanes with 5 to 12 C atoms or 60 to 90% by weight of cyclohexane and in each case 10 to 40% by weight of benzene or dichlorobenzene are very particularly preferred for formation of the lipophilic phase.

The extraction can be carried out in customary extractors, such as mixer/separators, perforated tray extractors, pulsed perforated tray extractors or rotating disc extractors.

The amounts of hydrophilic and lipophilic phase required for the extraction depend on the solubility of the components to be separated. The amount of hydrophilic and lipophilic phase is preferably as low as possible, that is to say just sufficient to dissolve all of the mixture to be separated. The weight ratio of lipophilic to hydrophilic phase is generally 1:1 to 5:1, preferably 2:1 to 4:1.

The water content of the mixtures which are very particularly preferably to be used for formation of the hydrophilic phase depends on the solubility of the polyglycidyl compound in this phase. For polyglycidyl compounds of relatively good solubility, for example those contained in mixtures from the reaction of diallyl esters of malonic or maleic acid with percarboxylic acids, the water content of the hydrophilic phase is preferably 40 to 50% by weight. It is thereby possible to keep the amount of lipophilic phase low. It can be reduced even further if the lipophilic phase contains aromatics.

For polyglycidyl compounds of poorer solubility, the amount of methanol or N-methylpyrrolidone in the hydrophilic phase is preferably as high as possible, as is the content of aromatics in the lipophilic phase, it being ensured that a miscibility gap between the lipophilic and hydrophilic phase and a sufficiently high separation factor remain.

If the optimum composition of the hydrophilic and lipophilic phase, that is to say the best combination of a high separation factor and low volume of the phase, is to be determined in preliminary experiments for extractive separation of a particular mixture, only the separation of the completely epoxidised polyallyl compound (=polyglycidyl compound) from the partially epoxidized polyallyl compound still containing one allyl group need be taken into consideration. The unreacted polyallyl compounds and those with a lower degree of epoxidation do not have to be separated from one another and their extraction properties are similar to those of the partially epoxidized polyallyl compounds still containing one allyl group.

The reaction is in general carried out at normal temperature. However, it is also possible to carry out the extraction at reduced or elevated temperature, for example at temperatures in the range from 10° to 60° C.

The laden lipophilic phase and the laden hydrophilic phase are worked up separately in a manner which is known per se. The unladen phases are recovered from the laden lipophilic phase and the laden hydrophilic phase by separate distillation and are recycled to the extraction. These distillations can be carried out, for example, under a pressure in the range from 10 to 150 mbar at a bottom temperature in the range from 90° to 140° C. The residue thereby obtained from the lipophilic phase, which contains unreacted polyallyl compound, partially epoxidized polyallyl compounds and, where relevant, small amounts of completely epoxidized polyallyl compounds (=polyglycidyl compounds), can be recycled to the reaction with the percarboxylic acid, after addition of fresh polyallyl compound. The addition of fresh polyallyl compound can also be effected directly in the reaction vessel. In particular cases, for example if a solid residue is obtained after distillation of the reaction mixture to remove the carboxylic acid, it may be advantageous to add the fresh polyallyl compound already to the bottom product of this distillation and to feed the bottom product of this distillation to the extraction, together with the fresh polyallyl compound.

The desired polyglycidyl compounds are obtained as the residue from the distillation of the laden hydrophilic phase. According to the invention, it is possible to isolate these polyglycidyl compounds in high yields and purities.

The process according to the invention has a number of advantages. Compared with the applications of the Prileschajew reaction described above, a particular advantage of the process according to the invention is that the carboxylic acid formed from the percarboxylic acid can be removed from the reaction mixture by measures which give rise to no salt-containing effluents which pollute the environment. It is not necessary to use a catalyst, for example an ion exchanger or aluminum oxide, during the reaction. Compared with the publications cited, it is possible, by the process according to the invention, to prepare and isolate polyglycidyl compounds economically in a controlled manner. The process according to the invention can be carried out as a cyclic process, with which it is possible to separate off the nonepoxidised and partially epoxidised polyallyl compounds, which are always obtained together with the completely epoxidised polyallyl compounds, and to react them again with percarboxylic acids. Many of the polyglycidyl compounds accessible according to the invention cannot be isolated by distillation under industrial conditions because of their high boiling points and their readiness to undergo polymerisation.

By the process according to the invention, it is possible to prepare and isolate high yields of the polyglycidyl compounds in a controlled manner in a particularly economic process suitable for large-scale industrial applications, with a combination of distillation and extraction under mild conditions.

In the following examples, which illustrate the process according to the invention in more detail but do not restrict it, the percentages are by weight, unless indicated otherwise.

EXAMPLES

The following abbreviations are used in the examples:
DA for diallyl hexahydrophthalate
AG for allyl glycidyl hexahydrophthalate
DG for diglycidyl hexahydrophthalate

EXAMPLE 1

12.6 kg (50 mol) of DA are initially introduced into a 60 liter stirred reactor with a double-walled jacket, internal cooling coils and reflux condenser and were warmed to 60° C. 28.81 kg of a 20% strength solution of perpropionic acid in benzene (64 mol) were pumped in, while stirring. The perpropionic acid solution contained less than 0.1% of water, less than 0.2% of hydrogen peroxide and less than 10 ppm of mineral acid, and was added such that the temperature could be maintained at 60° C. Stirring was then continued at this temperature. Samples were taken from the reaction mixture at intervals of time, and the content of perpropionic acid still present at the particular point in time was determined by titration, and the formation of epoxides or the decrease in epoxidizable double bonds was determined by gas chromatography by comparison with an internal standard.

After a reaction time of 5 hours, the perpropionic acid conversion was 97.2% and the DA conversion was 84.8%. AG was formed with a selectivity of 53.2% and DG was formed with a selectivity of 39.1%, in each case based on the DA reacted.

After addition of 8.2 kg of dichlorobenzene, the benzene, propionic acid and dichlorobenzene were removed as a joint head product in a packed column operated with a falling stream evaporator under a pressure of 150 mbar. This top product was separated into the pure components in a further column. A mixture composed of 8% of dichlorobenzene, 13.0% of DA, 41.1% of AG and 32.1% of DG remained as the bottom product. 4 g of this bottom product were shaken with 10 g of a mixture consisting of 70% of methanol and 30% of water (hydrophilic phase) and with 20 g of a mixture consisting of 80% of n-heptane and 20% of benzene (lipophilic phase) in a separating funnel. After separation of the phases, the two phases were analyzed by gas chromatography, the following contents being obtained:

|    | hydrophilic phase | lipophilic phase |
|----|-------------------|------------------|
| DA | 0.46%             | 1.75%            |
| AG | 0.57%             | 4.22%            |
| DG | 8.03%             | 1.73%            |

This results in the following separation factor for the separation of AG and DG:

$$\beta = \frac{[AG]_{LP}}{[AG]_{HP}} \cdot \frac{[DG]_{HP}}{[DG]_{LP}} = 4.28$$

LP here denotes lipophilic phase;

HP here denotes hydrophilic phase; the square brackets denote the concentration of the substances shown therein.

DG was isolated by counter-current extraction with the aid of a pulsed perforated tray extractor with 70 actual trays. For this, 400 g per hour of the bottom product obtained above were pumped into the extractor at the 20th tray counted from the top. 1,000 g per hour of a mixture of methanol and water (70:30) were pumped in at the top tray and 2,000 g per hour of a mixture of heptane and benzene (80:20) were pumped in at the bottom tray. The methanol/water phase was taken off at the bottom and the heptane/benzene phase was taken off at the top. These phases had the following contents:

|    | Extractor top product (heptane/benzene phase) | Extractor bottom product (methanol/water phase) |
|----|----|----|
| DA | 2.32% | — |
| AG | 7.26% | 0.07% |
| DG | 1.11% | 9.37% |

Methanol and water were distilled off from the bottom product of the extractor as the joint top product in a thin film evaporator, and were recycled to the extractor. DG remained in the form of a light yellow oil containing less than 1% of AG.

Heptane and benzene were distilled off from the top product of the extractor as the joint top product in a falling film evaporator under 150 mbar and were recycled to the extractor. A mixture containing DA, AG and DG remained as the bottom product. After addition of fresh DA, this was recycled again to the reaction with perpropionic acid solution.

The solvent mixtures recycled to the reactor had the following composition:

|  | Heptane/benzene mixture | Methanol/water mixture |
|---|---|---|
| Heptane | 77.7% | 0.7% |
| Benzene | 19.6% | 2.3% |
| Methanol | 2.55% | 67.0% |
| Water | 0.15% | 30.0% |

EXAMPLE 2

A mixture containing 11.4% of DA, 44.9% of AG and 35.8% of DG was obtained in a manner analogous to that in Example 1 by reacting 12.6 kg (50 mol) of DA with 31.5 kg of a 20% strength solution of perpropionic acid in benzene (=70 mol of perpropionic acid) at 60° C. for 6 hours and subsequently distilling the reaction mixture, after addition of dichlorobenzene.

4 g of this mixture were shaken with 12 g of a mixture of 70% of methanol and 30% of water (hydrophilic phase) and 24 g of cyclohexane (lipophilic phase) in a separating funnel. After separation of the phases, the two phases were analysed by gas chromatography, the following contents being obtained:

|    | hydrophilic phase | lipophilic phase |
|----|----|----|
| DA | 0.28% | 1.79% |
| AG | 3.47% | 4.21% |
| DG | 5.05% | 1.27% |

This results in a separation factor of $\beta=4.8$ for the separation of AG and DG.

On extractive working up of the mixture, which was carried out according to Example 1 with 400 g/hour of the DA/AG/DG mixture, 1,200 g/hour of a methanol/water mixture (70:30) and 2,400 g/hour of cyclohexane, 81% of the DG present in the mixture was separated off. The DG separated off contained 1% of AG.

EXAMPLE 3

4 g of the same mixture as in Example 2 were dissolved in 10 g of methanol/water (70:30) and were shaken with 20 g of a mixture consisting of 80% of heptane and 20% of tetrahydrofuran in a separating funnel. After separation of the phases, the two phases were analysed by gas chromatography, a separation factor of $\beta=4.9$ resulting.

On extractive working up of the mixture, which was carried out according to Example 1 with 400 g/hour of the DA/AG/DG mixture, 1,000 g/hour of a methanol/water mixture (70:30) and 2,000 g/hour of a heptane/tetrahydrofuran mixture (80:20), 79% of the DG present in the mixture were separated off. The DG separated off contained 0.9% of AG.

The unladen lipophilic phase was recovered from the laden lipophilic phase by distillation and recycled to the extractor. After addition of fresh DA, the bottom product of this distillation was recycled to the reactor.

EXAMPLE 4

4 g of the same mixture as in Example 2 were shaken with 20 g of a mixture of heptane/benzene (80:20) as the lipophilic phase and with 10 g of a mixture of diethylene glycol/water (80:20) as the hydrophilic phase in a separating funnel. After separation of the phases, the two phases were analysed by gas chromatography. A separation factor of $\beta=5.1$ resulted for the separation of AG and DG.

On extractive working up of the mixture, which was carried out according to Example 1 with 400 g/hour of the DA/AG/DG mixture, 2,000 g/hour of a heptane/benzene mixture (80:20) and 1,000 g/hour of a diethylene glycol/water mixture (80:20), 78% of the DG present in the mixture was separated off. The DG separated off contained 0.8% of AG.

EXAMPLE 5

10 g of the same mixture as in Example 2 were shaken with 5 g of a mixture consisting of N-methylpyrrolidone and water (70:30), as the hydrophilic phase, and 15 g of cyclohexane as the lipophilic phase in a separating funnel. After separation of the phases, the two phases were analysed by gas chromatography, a separation factor of $\beta=4.6$ resulting for the separation of AG and DG.

On extractive working up of the mixture, which was carried out according to Example 1 with 1,000 g/hour of the DA/AG/DG mixture, 500 g/hour of an N-methylpyrrolidone/water mixture (70:30) and 1,500 g/hour of cyclohexane, 77.5% of the DG present in the mixture was separated off. The DG separated off contained 0.7% of AG.

EXAMPLE 6

10 g of the same mixture as in Example 2 were shaken with 5 g of a mixture consisting of sulpholane and water (80:20), as the hydrophilic phase, and 15 g of cyclohexane as the lipophilic phase in a separating funnel. After separation of the phases, the two phases were analyzed by gas chromatography, a separation factor $\beta$ of 5.3 resulting for the separation of AG from DG.

On extractive working up of the mixture, which was carried out according to Example 1 with 1,000 g/hour of the DA/AG/DG mixture, 500 g/hour of a sulpholane/water mixture (80:20) and 1,500 g/hour of cyclohexane, 80.5% of the DG present in the mixture was separated off. The DG separated off contained 1% of AG.

EXAMPLE 7

12.3 kg (50 mol) of diallyl phthalate were reacted with 27.042 kg of a 21.3% strength solution of perpropionic acid in benzene (64 mol) at 60° C. as described in Example 1. After a reaction time of 7 hours, a peracid conversion of 96.9% resulted. The conversion of diallyl phthalate was 85.5%. Allyl glycidyl phthalate was formed with a selectivity of 51.8% and diglycidyl phthalate was formed with a selectivity of 42.3%, in each case based on the diallyl ester reacted.

After addition of 8 kg of dichlorobenzene, working up was carried out as described in Example 1. After removal of the benzene and propionic acid, a mixture composed of 6% of dichlorobenzene, 13.1% of diallyl phthalate, 41.2% of allyl glycidyl phthalate and 34.8% of diglycidyl phthalate resulted.

4 g of this mixture were extracted by shaking with 10 g of a mixture consisting of 65% of methanol and 35% of water (hydrophilic phase) and 20 g of cyclohexane (lipophilic phase) in a separating funnel. After separation of the phases, the two phases were analyzed by gas chromatography, a separation factor of $\beta=4.8$ resulting for the separation of allyl glycidyl phthalate from diglycidyl phthalate.

The mixture containing dichlorobenzene, diallyl phthalate, allyl glycidyl phthalate and diglycidyl phthalate was separated by extraction in a manner corresponding to that described in Example 1. 400 g/hour of the ester mixture, 1,000 g/hour of a methanol/water mixture (65:35) and 2,000 g/hour of cyclohexane were used for this. 78% of the diglycidyl phthalate contained in the ester mixture were separated off from the methanol/water phase, the product containing less than 1% of allyl glycidyl phthalate. A mixture composed of 5.4% of dichlorobenzene, 19.5% of diallyl phthalate, 61.4% of allyl glycidyl phthalate and 11.4% of diglycidyl phthalate were separated off from the cyclohexane phase and, after addition of fresh diallyl phthalate, was recycled again to the reaction with a solution of perpropionic acid in benzene.

EXAMPLE 8

12.6 kg (50 mol) of diallyl hexahydroterephthalate were reacted with 26.79 kg of a 21.5% strength solution of perpropionic acid in benzene (64 mol) at 60° C. by the procedure described in Example 1. After a reaction time of 7 hours, a peracid conversion of 97.1% resulted. The conversion of diallyl hexahydroterephthalate was 85%. Allyl glycidyl hexahydroterephthalate was formed with a selectivity of 52.8% and diglycidyl hexahydrophthalate was formed with a selectivity of 39.6%, in each case based on the diallyl hexahydroterephthalate reacted.

After addition of 8.5 kg of dichlorobenzene, the benzene, propionic acid and dichlorobenzene were distilled off as a joint top product in a manner corresponding to that described in Example 1. A bottom product containing 6.4% of dichlorobenzene, 13.0% of diallyl hexahydroterephthalate, 42.2% of allyl glycidyl hexahydroterephthalate and 32.2% of diglycidyl hexahydroterephthalate was thereby obtained. 10 g of this mixture were shaken with 15 g of a mixture of 70% of N-methylpyrrolidone and 30% of water (hydrophilic phase) and with 30 g of a mixture of 60% of cyclohexane and 40% of dichlorobenzene (lipophilic phase) in a separating funnel. After separation of the phases, the two phases were analyzed by gas chromatography, a separation factor of $\beta=5.3$ resulting for the separation of allyl glycidyl hexahydroterephthalate from diglycidyl hexahydroterephthalate.

Extractive separation of the ester mixture was carried out in a manner corresponding to that described in Example 1. For this, 1 kg of the ester mixture, 3 kg of a mixture of 60% of cyclohexane and 40% of dichlorobenzene and 1.5 kg of a mixture of 70% of N-methylpyrrolidone and 30% of water were pumped per hour into the extractor.

85% of the diglycidyl hexahydroterephthalate contained in the ester mixture were separated off from the hydrophilic phase. This product contained 1.5% of allyl glycidyl hexahydroterephthalate.

EXAMPLE 9

9.9 kg (50 mol) of diallyl succinate were reacted with 28.9 kg of a 21.8% strength solution of perpropionic acid in benzene (70 mol) at 60° C. in a manner corresponding to that described in Example 1. After a reaction time of 8 hours, a peracid conversion of 97.0% and a conversion of diallyl succinate of 88% resulted. Allyl glycidyl succinate was formed with a selectivity of 46.3% and diglycidyl succinate was formed with a selectivity of 46.1%, in each case based on the diallyl succinate reacted.

After addition of 6 kg of dichlorobenzene, the benzene and propionic acid were distilled off, together with the dichlorobenzene, by a procedure corresponding to that described in Example 1. A mixture composed of 7.8% of dichlorobenzene, 10.0% of diallyl succinate, 37.7% of allyl glycidyl succinate and 37.3% of diglycidyl succinate remained.

10 g of this ester mixture was shaken with 20 g of a mixture of 55% of methanol and 45% of water (hydrophilic phase) and 40 g of a mixture of 75% of cyclohexane and 25% of benzene (lipophilic phase) in a separating funnel. After separation of the phases, the two phases were analysed by gas chromatography, a separation factor $\beta$ of 6.8 resulting for the separation of allyl glycidyl succinate from diglycidyl succinate.

Extractive working up of the ester mixture was carried out in a manner corresponding to that described in Example 1. For this, 600 g of the ester mixture, 1.2 kg of a methanol/water mixture (55:45) and 2.4 kg of a cyclohexane/benzene mixture (75:25) per hour were fed to the extractor. 78% of the diglycidyl succinate contained in the ester mixture was isolated from the hydrophilic phase. This product contained 0.9% of allyl glycidyl succinate.

EXAMPLE 10

9.8 kg (50 mol) of diallyl maleate were reacted with 28.9 kg of a 21.8% strength solution of perpropionic acid in benzene (70 mol) at a reaction temperature of 60° C. in a manner analogous to that described in Example 1. After a reaction time of 8.5 hours, the percarboxylic acid conversion was 97.2%. The conversion of diallyl maleate was 88.3%. Allyl glycidyl maleate was formed with a selectivity of 45.8% and diglycidyl maleate was formed with a selectivity of 44.7%, in each case based on the diallyl maleate reacted.

After addition of 6 kg of dichlorobenzene, the benzene, propionic acid and dichlorobenzene were distilled off as a joint top product in a manner analogous to that described in Example 1. A mixture composed of 6.5% of dichlorobenzene, 10.3% of diallyl maleate, 37.3% of allyl glycidyl maleate and 37.0% of diglycidyl maleate remained in the bottom of the column.

10 g of this ester mixture were extracted by shaking with 20 g of a mixture consisting of 57.5% of methanol and 42.5% of water (hydrophilic phase) and with 40 g of a mixture consisting of 70% of cyclohexane and 30% of dichlorobenzene (lipopilic phase) in a separating funnel. After separation of the phases, the two phases were analyzed by gas chromatography, a separation factor of $\beta=5.6$ resulting for the separation of allyl glycidyl maleate from diglycidyl maleate.

Extractive working up of the ester mixture was carried out in a manner analogous to that described in Example 1. 600 g of the ester mixture, 1.2 kg of a mixture of 57.5% of methanol and 42.5% of water and 2.4 kg of a mixture of 70% of cyclohexane and 30% of dichlorobenzene per hour were fed to the extractor. 82% of the diglycidyl maleate contained in the ester mixture was isolated from the methanol/water phase. This product contained less than 0.8% of allyl glycidyl maleate.

EXAMPLE 11

9.8 kg (50 mol) of diallyl fumarate were reacted with 26.18 kg of a 22% strength solution of perpropionic acid in benzene (64 mol) at 60° C. in a manner analogous to that described in Example 1. After a reaction time of 6.8 hours, a percarboxylic acid conversion of 96.8% resulted. The conversion of diallyl fumarate was 90%. Allyl glycidyl fumarate was formed with a selectivity of 46.2% and diglycidyl fumarate was formed with a selectivity of 42.3%, in each case based on the diallyl fumarate reacted.

After addition of 12 kg of dichlorobenzene, the benzene, propionic acid and dichlorobenzene were distilled off as a joint top product in a manner analogous to that described in Example 1. A mixture composed of 34% of dichlorobenzene, 6.5% of diallyl fumarate, 26.2% of allyl glycidyl fumarate and 23.9% of diglycidyl fumarate remained.

10 g of this ester mixture were extracted by shaking with 24 g of a mixture consisting of 75% of N-methylpyrrolidone and 25% of water (hydrophilic phase) and with 22 g of a mixture consisting of 65% of cyclohexane and 35% of dichlorobenzene (lipophilic phase) in a separating funnel. After separation of the phases, the two phases were analyzed by gas chromatography, a separation factor of $\beta=4.2$ resulting for the separation of allyl glycidyl fumarate from diglycidyl fumarate.

Extractive working up of the ester mixture was carried out in a manner corresponding to that described in Example 1, 600 g of the ester mixture, 1.5 kg of a mixture of N-methylpyrrolidone and water (75:25) and 2.5 kg of a mixture of cyclohexane and dichlorobenzene (65:35) per hour being fed to the extractor.

82% of the diglycidyl fumarate contained in the ester mixture was obtained from the N-methylpyrrolidone/water phase as a crystalline product containing less than 1% of allyl glycidyl fumarate.

EXAMPLE 12

6.895 kg (35 mol) of trisallylurazole were reacted with 31.5 kg of a 22% strength solution of perpropionic acid in benzene (77 mol) at 60° C. in a manner analogous to that described in Example 1. After a reaction time of 10 hours, the percarboxylic acid conversion was 97.2% and the conversion of trisallylurazole was 94.6%. Diallylglycidylurazole was formed in a selectivity of 28.3%, allyldiglycidylurazole was formed in a selectivity of 41.2% and trisglycidylurazole was formed with a selectivity of 20.1%, in each case based on the trisallylurazole reacted.

After addition of 8 kg of dichlorobenzene, the benzene, propionic acid and dichlorobenzene were distilled off as a joint top product according to Example 1. A mixture composed of 50% of dichlorobenzene, 2.3% of trisallylurazole, 12.4% of diallylglycidylurazole, 20.0% of allyldiglycidylurazole and 10.1% of trisglycidylurazole resulted as the bottom product.

10 g of this mixture were shaken with 7.5 g of a mixture consisting of 20% of methanol and 80% of water (hydrophilic phase) and with 12.5 g of dichlorobenzene (lipophilic phase) in a separating funnel. After separation of the phases, the two phases were analysed by gas chromatography, a separation factor of $\beta=3.6$ resulting from the separation of allyldiglycidylurazole from trisglycidylurazole.

Extractive working up of the mixture was carried out in a manner analogous to that described in Example 1, 1 kg per hour of the mixture being fed to the top third of the extractor, 0.75 kg per hour of a mixture of 20% of methanol and 80% of water being fed in at the top tray of the reactor and 1.25 kg per hour of dichlorobenzene being fed in at the bottom tray of the extractor. 72% of the trisglycidylurazole contained in the mixture was isolated from the methanol/water phase, the product still containing 4.8% of allyldiglycidylurazole.

What is claimed is:

1. A process for the preparation of a polyglycidyl compound which comprises contacting diallyl hexahydrophthalate with a percarboxylic acid containing 3 or 4 carbon atoms, removing carboxylic acid formed from the percarboxylic acid by distilling the resultant reaction mixture to distill off said carboxylic acid to leave behind a mixture of unreacted diallyl hexahydrophthalate and epoxidized reaction product, contacting said mixture simultaneously with a lipophilic phase comprising n-heptane and benzene and a hydrophilic phase comprising methanol and water, removing said lipophilic phase from said hydrophilic phase, working up the resultant laden lipophilic phase, working up the resultant hydrophilic phase and obtaining a polyglycidyl compound from said laden hydrophilic phase.

2. A process according to claim 1, wherein said percarboxylic acid is employed in an amount of 0.6 to 1.1 mol per mol of double bond of the polyallyl compound to be epoxidized.

3. A process according to claim 1, wherein said percarboxylic acid is employed in the form of a solution in an organic solvent which solution contains less than 10% by weight of water, less than 1% by weight of hydrogen peroxide and less than 50 ppm of mineral acid.

4. A process according to claim 1, wherein said carboxylic acid formed from said percarboxylic acid is removed by distillation which is carried out in the presence of a solvent having a boiling point between that of the carboxylic acid and that of the polyallyl compound.

5. A process according to claim 1, wherein the weight ratio of lipophilic to hydrophilic phase is 1–5:1.

6. A process according to claim 1, wherein the extraction with the lipophilic phase and hydrophilic phase is carried out at a temperature in the range from 10° to 60° C.

7. A process according to claim 1, wherein to the mixture left behind following distillative removal of the carboxylic acid formed from the percarboxylic added there is added fresh polyallyl compound and said polyallyl compound together with said mixture are subjected to extraction simultaneously with said lipophilic phase and said hydrophilic phase.

8. A process according to claim 1, wherein the laden lipophilic phase is subjected to distillation to distillatively remove lipophilic phase which is recycled to said extraction to leave behind a mixture of unreacted polyallyl compound and polyallyl compound which has been partially epoxidized and said mixture of unreacted polyallyl compound and partially epoxidized polyallyl compound is recycled to reaction with said percarboxylic acid.

* * * * *